US008235883B2

(12) United States Patent
Iske et al.

(10) Patent No.: US 8,235,883 B2
(45) Date of Patent: Aug. 7, 2012

(54) SHARPS DISPOSAL SYSTEM

(75) Inventors: Mark L. Iske, Missouri City, TX (US); Ronald E. Pierce, Sugar Land, TX (US)

(73) Assignee: Sharps Compliance, Inc., Houston, TX (US)

( * ) Notice: Subject to any disclaimer, the term of this patent is extended or adjusted under 35 U.S.C. 154(b) by 55 days.

(21) Appl. No.: 12/258,279

(22) Filed: Oct. 24, 2008

(65) Prior Publication Data
US 2009/0120820 A1  May 14, 2009

Related U.S. Application Data

(63) Continuation of application No. 11/530,024, filed on Sep. 7, 2006, which is a continuation of application No. 10/713,419, filed on Nov. 14, 2003, now abandoned.

(51) Int. Cl.
*B65D 83/10* (2006.01)
*B65D 43/18* (2006.01)
*B65D 43/14* (2006.01)

(52) U.S. Cl. ........ 588/249; 206/363; 206/365; 220/822; 220/833

(58) Field of Classification Search .......... 206/363–366, 206/370; 220/908; 604/110, 403
See application file for complete search history.

(56) References Cited

U.S. PATENT DOCUMENTS

| | | | | |
|---|---|---|---|---|
| 3,134,538 A * | 5/1964 | Fibus | ............... | 232/17 |
| 3,204,866 A * | 9/1965 | Brighton et al. | ............. | 232/43.2 |
| 3,797,643 A * | 3/1974 | Shupp | ........... | 294/165 |
| 4,576,281 A * | 3/1986 | Kirksey | ........... | 206/370 |
| 4,662,516 A * | 5/1987 | Baker et al. | ............ | 206/363 |
| 5,058,764 A * | 10/1991 | Gaba | ............... | 220/481 |
| 5,413,243 A * | 5/1995 | Bemis et al. | ............ | 220/481 |
| 5,419,435 A * | 5/1995 | Perzan et al. | ........... | 206/366 |
| 5,423,450 A * | 6/1995 | Shillington et al. | ........ | 220/481 |
| 5,630,506 A * | 5/1997 | Thorne et al. | ........... | 206/366 |
| 5,647,502 A * | 7/1997 | Marsh | ........... | 220/481 |
| 6,010,444 A * | 1/2000 | Honeycutt et al. | ......... | 588/255 |
| 6,332,554 B1 * | 12/2001 | McCarthy | .......... | 220/554 |

* cited by examiner

*Primary Examiner* — J. Gregory Pickett
*Assistant Examiner* — Andrew Perreault
(74) *Attorney, Agent, or Firm* — Robert W Strozier

(57) ABSTRACT

A sharps disposal system for safely collecting and disposing of medical sharps includes a cabinet defining an enclosure for receiving a removable used sharps receptacle therein. The cabinet includes a passageway through which sharps may be deposited in the sharps receptacle. A single lock, double door design facilitates safe removal and disposal of sharps deposited in the sharps receptacle.

3 Claims, 4 Drawing Sheets

FIG.6
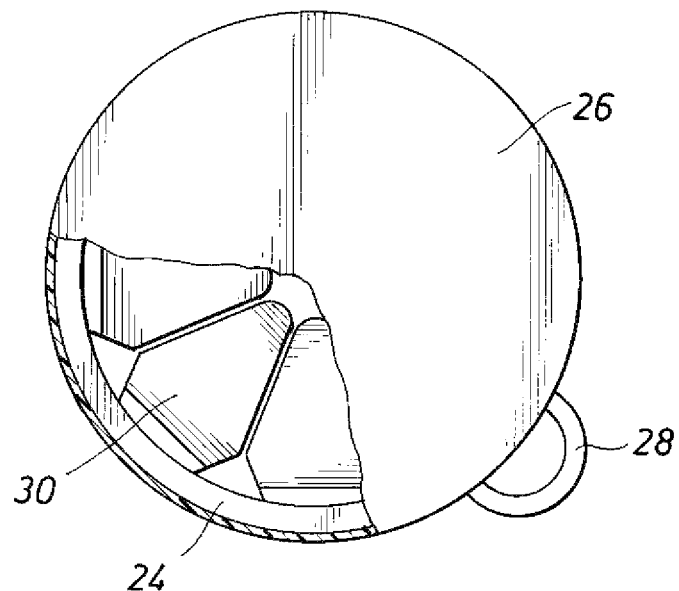
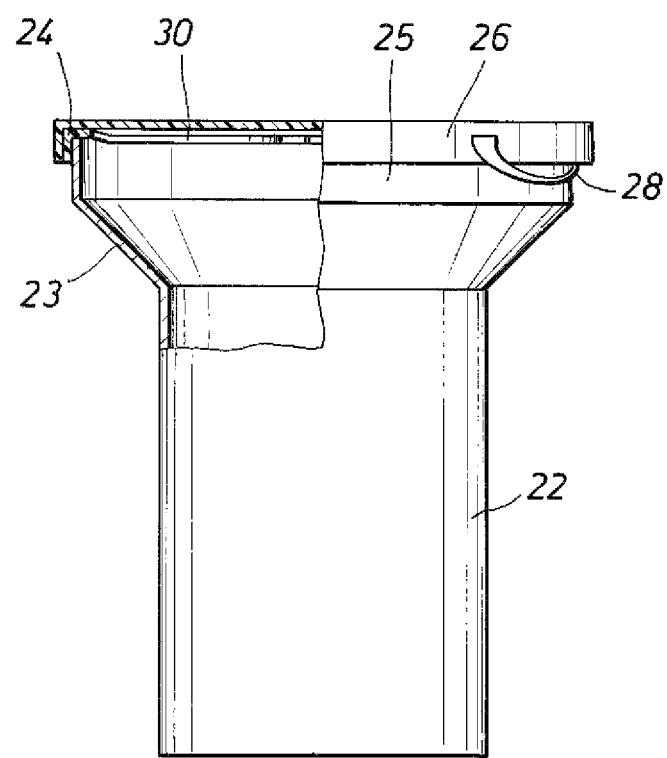
FIG.7

SHARPS DISPOSAL SYSTEM

RELATED APPLICATIONS

This application is a continuation of U.S. patent application Ser. No. 11/530,024 filed Sep. 7, 2006, pending, which is a continuation of U.S. patent application Ser. No. 10/713,419 filed Nov. 14, 2003, now abandoned.

BACKGROUND OF THE INVENTION

1. Field of the Invention

The present invention generally relates to containers for safely collecting, storing and transporting used hypodermic needles (sharps). The present invention specifically relates to safely collecting, storing and transporting used needles in non-traditional healthcare facilities, such as public non-healthcare settings.

2. Description of the Related Art

Disposal of sharps such as hypodermic needles in non-regulated settings is a tremendous public health safety problem. All used sharps are considered hazardous bio-medical waste as they contain body fluids which have the potential to transmit diseases to anyone exposed to them through a stick or open wound. Regulated businesses, such as medical facilities, generate used sharps in the routine provision of services. Such regulated businesses have developed stringent policy procedures for the safe collection and disposal of used sharps. As a result, regulated businesses routinely require and provide convenient access to sharps disposal containers within their facilities. Because of their potentially dangerous nature, particularly with present concerns regarding accidental transmittal of infectious diseases via contact with used needles, typical sharps disposal containers are designed not only to permit disposal but also to prevent unintentional contact with sharps deposited in the container. In regulated business settings disposal of sharps into containers is managed by trained professional staff to maximize safety.

Unregulated businesses, however, generally do not have any developed policy procedures for the safe collection and disposal of used sharps, nor trained professionals to manage the disposal. Unlike regulated healthcare businesses, the disposal of sharps is not a direct result of services performed in a non-regulated business. Therefore, non-regulated businesses, including but not limited to, commercial, industrial and retail settings, are generally unprepared to safely collect and dispose of used sharps that may be generated on their premises. However, sharps are routinely used, disposed and found in non-regulated businesses. Approximately three percent (3%) of the U.S. population regularly self-inject prescription drugs using hypodermic needles. Often, self-injectors are away from home or a medical facility when a dose must be administered in non-regulated business settings and public places. In addition to legal self-injectors, an undetermined number of illicit drug users self-inject non-prescription drugs, also in public places. It is estimated that within the U.S. three billion used needles are disposed of annually in non-regulated settings and unsafely discarded into the public solid waste stream.

The present growing trend of self-injecting and providing healthcare away from regulated medical facilities significantly increases the potential for inadvertent handling of, or accidental contact with, used sharps, particularly hypodermic needles, in public places. Used needles discarded by self-injectors expose the general population to sharps unmanaged by healthcare professionals and the potential for transmittal of diseases though contact with hypodermic needles contaminated with bloodborne pathogens. In recognition of the needs of such self-injectors, and to protect employees and business customers, many commercial, industrial and retail businesses are beginning to purchase sharps collection containers to dispose of sharps found on their premises.

Sharps containers used in commercial, industrial and retail businesses are generally controlled and kept out of sight, and are used only when an employee finds a used hypodermic needle. Such an approach to safe guarding employees and customers from used sharps is reactive and inappropriate in that only the needles left in visible sight are captured by employees, who themselves are placed in a position of potential contact with hazardous bio-medical waste as they are required to retrieve used needles for disposal. It is widely known that the majority of used sharps disposed in public places are in open trash receptacles, exposing workers and the public to a dangerous health risk. Generally, non-regulated businesses in the commercial, industrial and retail sectors do not proactively provide self-injectors with a means of safely disposing of their used sharps.

It is therefore an object of the invention to provide a sharps disposal system for use by self injectors to safely dispose of their used sharps in such a manner where the container is safe, secure and is resistant to tampering by unauthorized individuals.

It is another object of the invention to provide a safe public sharps collection system comprised of two individual components, a lockable steel permanent wall mounted cabinet to house the sharps container and a disposable sharps container contained within the cabinet which can be safely disposed of only by authorized personnel.

It is another object of the invention to provide a secure wall mounted cabinet incorporating safety features including a sharps disposal conduit and single locking mechanism preventing unauthorized access, and a double door design to facilitate safe removal of the sharps container housed within the cabinet.

SUMMARY OF THE INVENTION

In accordance with the present invention, a cabinet for safely collecting and storing medical sharps defines an enclosure for receiving a removable sharps collection container (receptacle) therein. A bracket securely retains the sharps receptacle within the cabinet. The cabinet includes a conduit depending downward from the top thereof. The conduit is open at both ends. The lower end of the conduit interfaces with the removable receptacle thereby forming a passageway for discarded sharps to enter the sharps receptacle. The cabinet includes a single lock, double door design facilitating safe removal of the sharps receptacle housed within the cabinet.

BRIEF DESCRIPTION OF THE DRAWINGS

So that the manner in which the above recited features, advantages and objects of the present invention are attained can be understood in detail, a more particular description of the invention, briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 6 is a partially broken away top plan view of the sharps receptacle housed in the sharps disposal cabinet of the present invention; and FIG. 7 is a partially broken away side view of the sharps receptacle housed in the sharps disposal cabinet of the present invention.

DETAILED DESCRIPTION OF THE INVENTION

Figure 1:
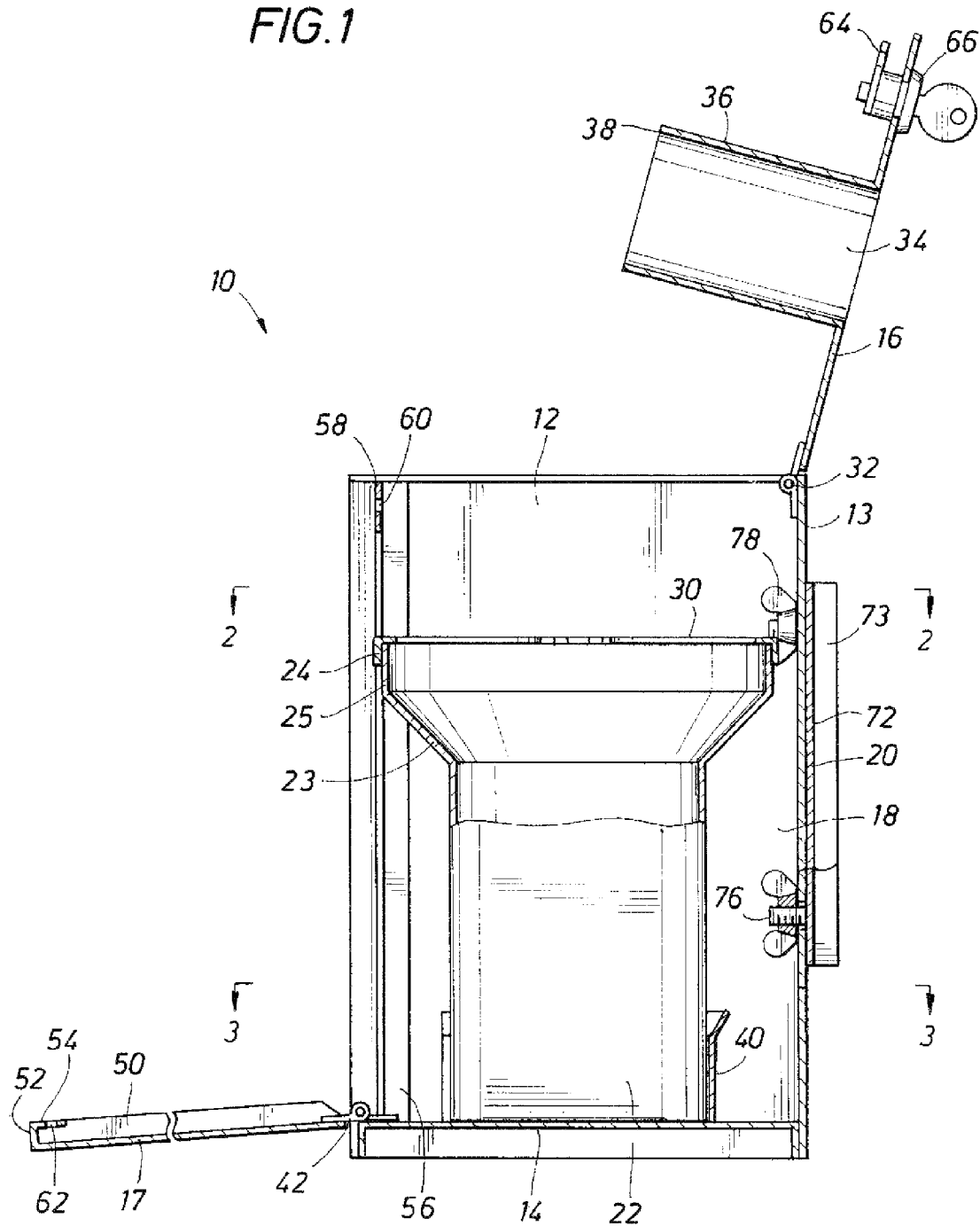
FIG. 1 is a section view of a sharps disposal system in accordance with the present invention depicting the sharps disposal cabinet in an open condition.

Referring first to FIG. 1, a sharps idisposal system in accordance with the present invention includes a sharps disposal cabinet generally identified by the reference numeral 10. The cabinet 10, fabricated of heavy gauge metal, includes a cabinet body formed by sidewalls 12, a back wall 13, a bottom 14, a top access door 16 and a side or front access door 17 which enclose an interior chamber 18. A mounting bracket 20 supports the cabinet 10 on a mounting surface, such as a wall or other suitable surface.

Figure 2:
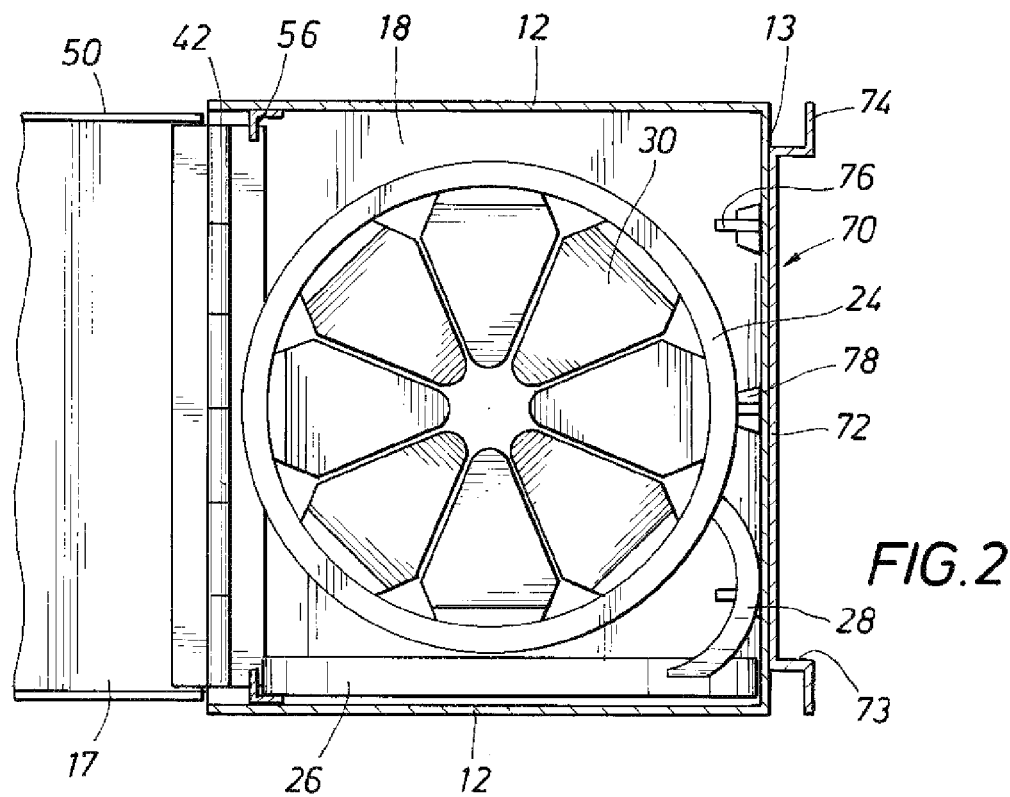
FIG. 2 is a partially broken away section view of the sharps disposal cabinet of the present invention taken along line 2-2 in FIG. 1.

A sharps receptacle 22 is housed within the chamber 18 of the cabinet 10. The receptacle 22 is preferably fabricated of puncture resistant material and includes a main body defining a substantially box-like profile. The body of the receptacle 22 includes an outwardly tapering portion 23 terminating in an upstanding lip 25 which circumscribes a circular opening forming the upper end of the receptacle 22. The open upper end of the receptacle 22 is closed by a circular lid 24. The planar surface of the lid 24 comprises a plurality of inwardly extending flexible tabs or fingers 30, as best shown in FIG. 2. The fingers 30 are connected to the circumferential edge of the lid 24 and extend radially inward toward the center of the lid 24. The fingers 30 extend across the open end of the receptacle 22 preventing the sharps deposited therein from spilling out when the receptacle 22 is removed from the cabinet 10. A snap-on cover 26 connected to the lid 24 by a flexible tether 28 is stored within the cabinet 10 adjacent to the receptacle 22 as shown in FIG. 2. Upon removal of the receptacle 22 from the cabinet 10 the cover 26 is snapped over the lid 24 thereby enclosing the discarded sharps therein for safe disposal.

Referring still to FIG. 1, the top access door 16 of the cabinet 10 is secured to the back wall 13 thereof by a hinge 32. The door 16 comprises a flat planar plate provided with a centrally located hole 34. A conduit, such as a cylinder 36 or the like, depends downwardly from the bottom surface of the door 16. The cylinder 36 is open at both ends. The proximal end of the cylinder 36 circumscribes the hole 34 and is welded or otherwise fixed to the door 16. The distal end 38 of the cylinder 36 projects into the chamber 18 of the cabinet 10 upon closure of the access door 16. The cylinder 36 is sized in length and diameter to minimize placing unintended items into the sharps disposal system of the invention and to prevent getting a finger or hand down into the sharps receptacle 22.

Figure 3:
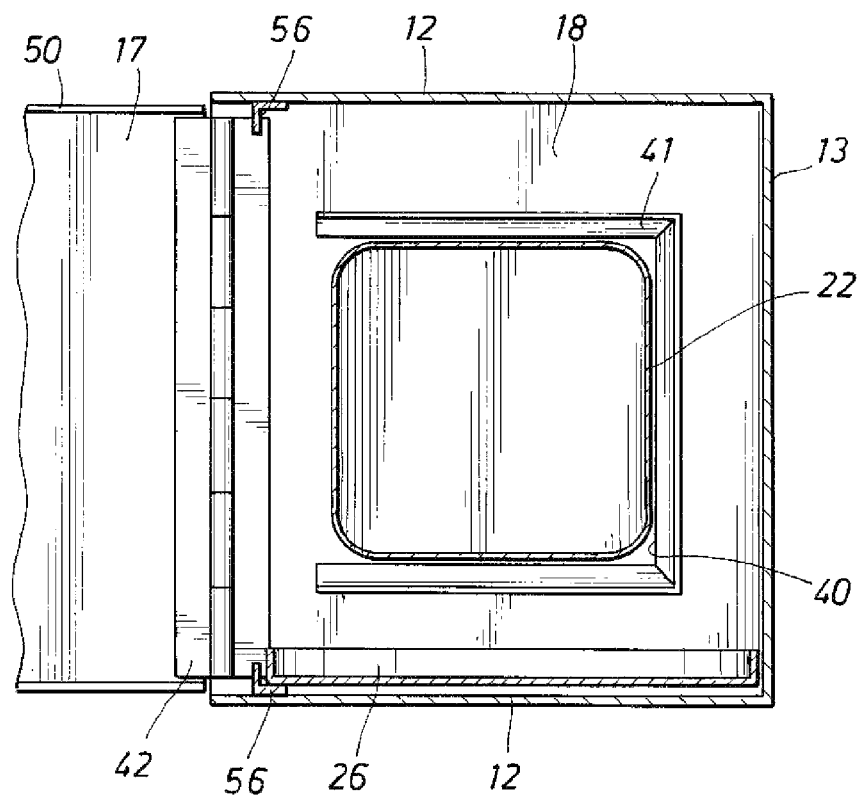
FIG. 3 is a partially broken away section view of the sharps disposal cabinet and sharps receptacle of the present invention taken along line 3-3 in FIG. 1.

Referring now to FIG. 3, the sharps receptacle 22 is shown housed within the chamber 18 of the cabinet 10. It is centrally located within the chamber 18 by a cradle bracket 40 fixed to the bottom 14 of the cabinet 10. In a preferred embodiment, the cradle bracket 40 is three-sided with the open side located opposite the access door 17. The bracket 40 is configured for frictionally engaging the bottom portion of the sharps receptacle 22 and positions the receptacle 22 to interface with the cylinder 36 upon closure of the top access door 16. It is understood that the bracket 40 may take the form of any suitable configuration for maintaining the sharps receptacle 22 within the cabinet 10 in cooperating alignment with the cylinder 36 depending downwardly from the top access door 16.

Referring again FIG. 1, the access door 17 is secured to the bottom 14 of the cabinet 10 by a hinge 42. The access door 17 comprises a flat planar plate having flange members 50 extending inwardly therefrom along opposite edges of the door 17. Along it upper end, the top edge of the door 17 extends inwardly defining a flat first surface 52 perpendicular to the door 17 and the distal end thereof projects downwardly defining a second surface 54 which is spaced from and parallel to the planar surface of the access door 17.

Structural reinforcement for the cabinet 10 is provided by right angle flanges 56 which are fixed along the sidewalls 12 and offset inwardly from the leading edges of the sidewalls 12. The flanges 56 are interconnected by a cross bar 58 extending across and connected to the upper ends of 10 the support flanges 56. A locking slot 610 is formed in the cross bar 58. The slot 60 is shaped to match the slot 62 formed in the surface 54 of the top edge of the access door 17. Upon closure of the door 17, the surface 54 of the access door 17 is in facing contact with the cross bar 58 and the lock slots 60 and 62 are in alignment for receiving the lock lever 64 of a lock 66 mounted on the top access door 16, as best shown in FIG. 4.

Figure 4:
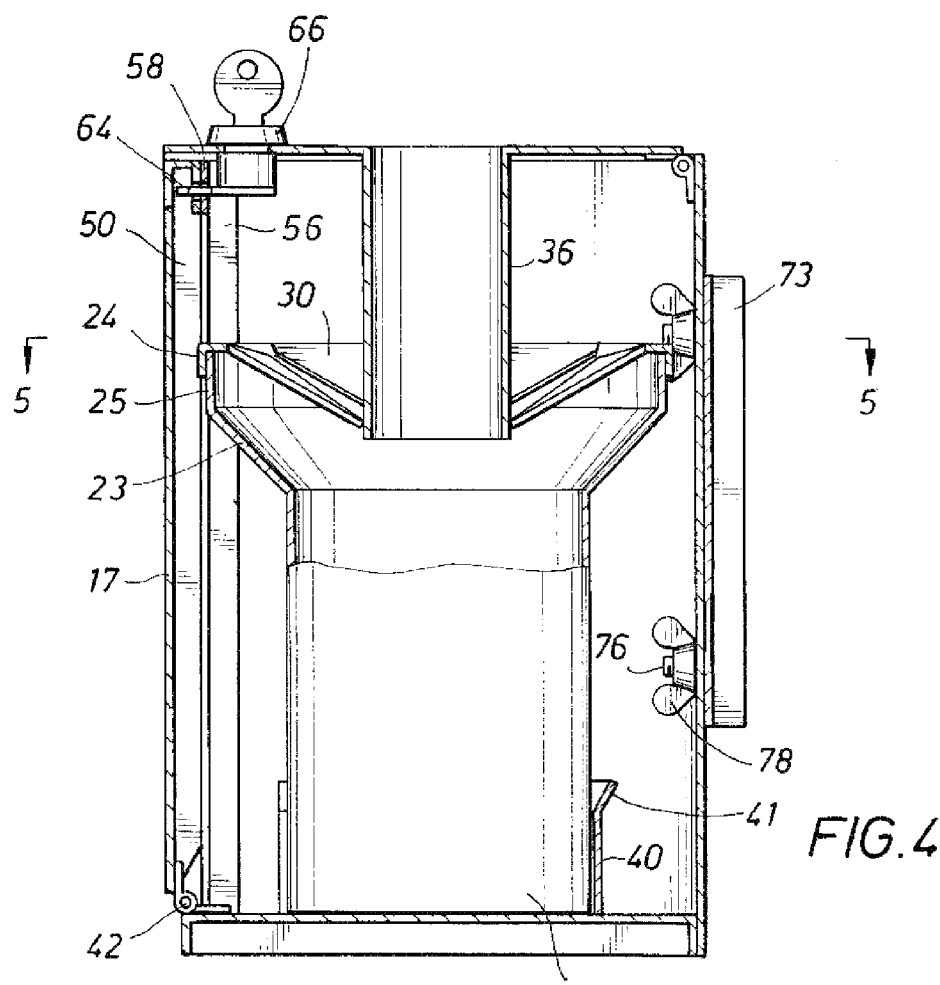
FIG. 4 is a section view of a sharps disposal system in accordance with the present invention depicting the sharps disposal cabinet in a closed condition.
Figure 5:
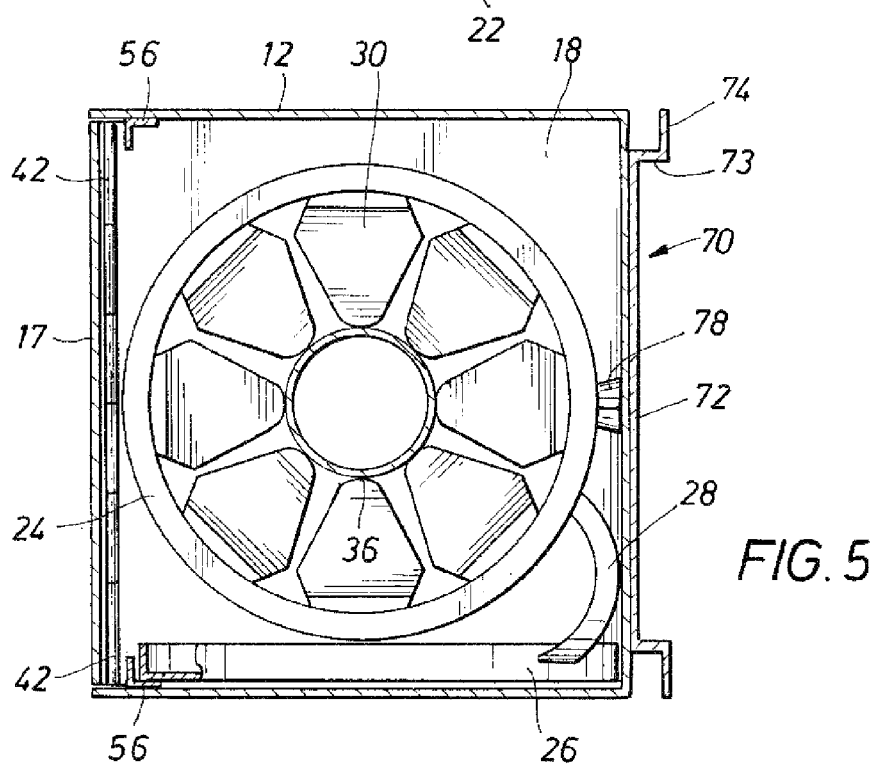
FIG. 5 is a section view of the sharps disposal cabinet of the present invention taken along line 5-5 in FIG. 4.

Referring now to FIGS. 4 and 5, the cabinet 10 is mounted to a mounting surface by a mounting bracket 70. The bracket 70 is si~bstantiallyU-shaped in cross-section as shown in FIG. 5. It includes a flat mounting plate 72 and mounting flanges 74 integrally formed therewith. Threaded posts 76 project from the mounting plate 72 and are received through corresponding holes formed in the back wall 13 of the cabinet 10. Wing nuts 78 secure the cabinet 10 to the mounting bracket 70.

So that the cabinet 10 is not easily removed from its mounting surface, the width of the mounting plate 72 is less than the width of the back wall 13 of the cabinet 10 so that it overlaps the mounting flanges 74. Thus, the bolts which secure the mounting bracket 70 (not shown in the drawings) to the mounting surface are covered and not accessible when the cabinet 10 is secured to the mounting bracket 70.

Referring still to FIG. 4, when the cabinet 10 is locked and the sharps receptacle 22 is contained in the chamber 18 thereof, the distal end of the cylinder 36 engages the flexible fingers 30 of the lid 24 pushing them downwardly and thereby forming an unobstructed passageway to the interior of the sharps receptacle 22. Sharps dropped through the hole 34 in the top access door 16 fall through the cylinder 36 into the sharps receptacle 22. The single lock, two door design of the cabinet 10 ensures that during removal of the receptacle 22 from the cabinet 10, personnel performing the task do not at any time place their hand over the top opening in the sharps receptacle 22. When the access door 16 is opened, the cylinder 36 rotates upwardly out of the way and the flexible fingers 30 return to their original orientation closing the opening created by the cylinder 36 in the lid 24. The access door 17 is opened and the receptacle 22 removed from the cabinet 10 and the cover 26 is snapped over the lid 24 of the receptacle 22, thereby enclosing the discarded sharps within the receptacle 22 for safe delivery to a facility for safely destroying the discarded sharps.

The foregoing disclosure and description of the invention are illustrative and explanatory thereof, and various changes in the invention may be made within the scope of the appended claims without departing from the spirit of the invention, and the scope thereof is determined by the claims which follow.

We claim:

1. A method of disposing of sharps comprising the steps of:
   placing a sharps receptacle having an opening in its top and a lid for covering the opening into an inner chamber of a substantially rigid locking cabinet in its opened state, where the cabinet comprises:
   a bottom, sidewalls and reinforcing flanges fixed to the sidewalls and offset inwardly for leading edges of the sidewalls and a cross bar including a cross bar slot fixed interconnecting the flanges;
   a first access door pivotally connected to a top edge of the cabinet and comprising a top of the cabinet and adapted to transition between a closed state and an opened state and including a hollow conduit centered in the first access door and depending downwardly from and welded to a bottom surface of the first access door and defining a hole in the first access door, where a distal end of the conduit extends into the opened end of the receptacle, where the conduit is sized in length and diameter to minimize placing unintended items into the sharps disposal system and to prevent getting a finger or hand down into the sharps receptacle and where the conduit rotates upwardly out of the way of the opened end of the receptacle, when the first access door is opened;
   a second access door pivotally connected to a side or bottom edge of the cabinet including a facing surface having a surface slot adapted to align with the cross bar slot when the second access doors is in a closed state to form aligned slots; and
   lock means for locking the two access doors of the cabinet including a lock lever, where the lock means transitions between a locked state, where the lock lever is received into the aligned slots and an unlocked state, where the lock lever rotates out of the aligned slots and where the lock means secures the cabinet from unauthorized tampering when in the locked state,
   where a portion of the doors contact each other when the doors are in their closed states and where the lock means is capable of locking the two doors simultaneously when the doors are in their closed states and the lock means is in its locked state,
   closing and locking the cabinet,
   disposing of medical sharps into the sharps receptacle within the inner chamber of the locked cabinet,
   unlocking the cabinet,
   removing the sharps receptacle containing the medical sharps,
   placing the lid over the opening of the sharps receptacle, and
   safely delivering the closed sharps receptacle containing the medical sharps to a facility for safely destroying the medical sharps.

2. A method of disposing of sharps comprising the steps of:
   placing a sharps receptacle having an opening in its top and a lid for covering the opening into an inner chamber of a substantially rigid locking cabinet in its opened state, where the cabinet includes:
   a bottom, sidewalls and reinforcing flanges fixed to the sidewalls and offset inwardly for leading edges of the sidewalls and a cross bar including a cross bar slot fixed interconnecting the flanges;
   a first access door pivotally connected to a top edge of the cabinet and comprising a top of the cabinet and adapted to transition between a closed state and an opened state and including a hollow conduit centered in the first access door and depending downwardly from and welded to a bottom surface of the first access door and defining a hole in the first access door, where a distal end of the conduit extends into the opened end of the receptacle, where the conduit is sized in length and diameter to minimize placing unintended items into the sharps disposal system and to prevent getting a finger or hand down into the sharps receptacle and where the conduit rotates upwardly out of the way of the opened end of the receptacle, when the first access door is opened;
   a second access door pivotally connected to a side or bottom edge of the cabinet including a facing surface having a surface slot adapted to align with the cross bar slot when the second access doors is in a closed state to form aligned slots; and
   lock means for locking the two access doors of the cabinet including a lock lever, where the lock means transitions between a locked state, where the lock lever is received into the aligned slots and an unlocked state, where the lock lever rotates out of the aligned slots and where the lock means secures the cabinet from unauthorized tampering when in the locked state,
   where a portion of the doors contact each other when the doors are in their closed states and where the lock means is capable of locking the two doors simultaneously when the doors are in their closed states and the lock means is in its locked state;
   closing and locking the cabinet,
   disposing of medical sharps into the sharps receptacle inside the inner chamber of the cabinet,
   unlocking the cabinet,
   opening the doors so that the hollow conduit rotates upward out of the way of the opening in the sharps receptacle,
   removing the sharps receptacle containing the medical sharps,
   placing the lid over the opening of the sharps receptacle, and
   safely delivering the closed sharps receptacle containing the medical sharps to a facility for safely destroying the medical sharps.

3. A method of disposing of sharps comprising the steps of:
   placing a sharps receptacle having an opening in its top and a lid for covering the opening into an inner chamber of a substantially rigid locking cabinet comprising
   a bottom, sidewalls and reinforcing flanges fixed to the sidewalls and offset inwardly for leading edges of the sidewalls and a cross bar including a cross bar slot fixed interconnecting the flanges;
   a first access door pivotally connected to a top edge of the cabinet and comprising a top of the cabinet and adapted to transition between a closed state and an opened state and including a hollow conduit centered in the first access door and depending downwardly from and welded to a bottom surface of the first access door and defining a hole in the first access door, where a distal end of the conduit extends into the opened end of the receptacle, where the conduit is sized in length and diameter to minimize placing unintended items into the sharps disposal system and to prevent getting a finger or hand down into the sharps receptacle and where the conduit rotates upwardly out of the way of the opened end of the receptacle, when the first access door is opened;

a second access door pivotally connected to a side or bottom edge of the cabinet including a facing surface having a surface slot adapted to align with the cross bar slot when the second access doors is in a closed state to form aligned slots; and lock means for locking the two access doors of the cabinet including a lock lever, where the lock means transitions between a locked state, where the lock lever is received into the aligned slots and an unlocked state, where the lock lever rotates out of the aligned slots and where the lock means secures the cabinet from unauthorized tampering when in the locked state, where a portion of the doors contact each other when the doors are in their closed states and where the lock means is capable of locking the two doors simultaneously when the doors are in their closed states and the lock means is in its locked state, closing and locking the cabinet, disposing of medical sharps into the sharps receptacle within the inner chamber of the locked cabinet, unlocking the cabinet, opening the doors so that the hollow conduit rotates upward out of the way of the opening in the sharps receptacle, removing the sharps receptacle containing the medical sharps, placing the lid over the opening of the sharps receptacle, and delivering the closed sharps receptacle containing the medical sharps to a facility for destruction.

\* \* \* \* \*